United States Patent [19]

Mitsuhashi et al.

[11] Patent Number: 5,599,954
[45] Date of Patent: Feb. 4, 1997

[54] N-SUBSTITUTED-7-AMINO-5-HYDROXY-3-OXOHEPTANOIC ACID DERIVATIVES AND METHOD FOR PRODUCING THE SAME

[75] Inventors: Sigeru Mitsuhashi; Tsukasa Sotoguchi; Yoshifumi Yuasa; Hidenori Kumobayashi, all of Kanagawa, Japan

[73] Assignee: Takasago International Corporation, Tokyo, Japan

[21] Appl. No.: 592,494

[22] Filed: Jan. 26, 1996

[30] Foreign Application Priority Data

Jan. 27, 1995 [JP] Japan ................................. 7011414

[51] Int. Cl.$^6$ ................................. C07D 315/00
[52] U.S. Cl. ........................ 549/419; 556/437; 560/41; 560/160; 560/170
[58] Field of Search ................................. 560/160, 170, 560/41; 556/437; 549/419

*Primary Examiner*—Michael L. Shippen
*Attorney, Agent, or Firm*—Sughrue, Mion, Zinn, Macpeak & Seas

[57] ABSTRACT

Compounds represented by the following general structural formula (1) and methods for producing the compounds:

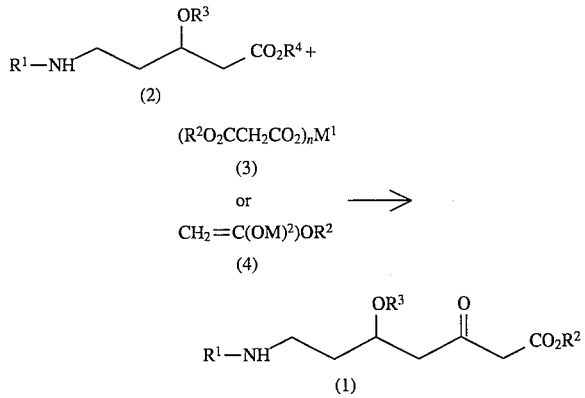

$R^1$ represents a group such as benzyloxycarbonyl, $R^2$ represents a lower alkyl group, $R^3$ represents a hydrogen atom or a protecting group, each of $M^1$ and $M^2$ represents a metal atom, and n represents the atomic valence of $M^1$. Intermediates for HMG-CoA reductase inhibitors can be prepared safely and easily from these compounds.

10 Claims, No Drawings

N-SUBSTITUTED-7-AMINO-5-HYDROXY-3-OXOHEPTANOIC ACID DERIVATIVES AND METHOD FOR PRODUCING THE SAME

BACKGROUND OF THE INVENTION

1. Field of the Invention

The present invention relates to N-substituted-7-amino-5-hydroxy-3-oxoheptanoic acid derivatives and a method for producing the same. These novel compounds are useful as synthetic intermediates for preparing 3-hydroxy-3-methylglutaryl coenzyme A (abbreviated as HMG-CoA below) reductase inhibitors known as antilipemic agents, namely, trans-6-[2-substituted pyrrole-1-yl )alkyl]-4-hydroxypyran-2-one derivatives, for example, (2R) -trans-5-[(4-fluorophenyl)-2-(1-methylethyl)-N-4-diphenyl]-1-[2-tetrahydro-4-hydroxy-6-oxo-2H-pyran-2-yl)ethyl]-1H-pyrrol-3-carboxyamide.

2. Description of the Related Art

Lactone residues which are considered to be the active sites of HMG-CoA reductase inhibitors, trans-6-[2-(substituted pyrrole-1-yl)alkyl]-4-hydroxypyran-2-one derivatives, have been synthesized via a series of steps from esters of 6-(2-aminoethyl)-2,2-dimethyl-1,3-dioxane-4-acetic acid having the general formula (5):

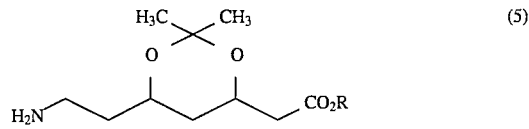

where R represents an alkyl group.

Furthermore, methods for producing these dioxane derivatives (5) which comprise reducing the cyano group in esters of 6-cyanomethyl-2,2-dimethyl-1,3-dioxane-4-acetic acid as a starting material, are disclosed in Japanese Patent Laid-Open No. 3-502798 corresponding to U.S. Pat. No. 5,003,080, Japanese Patent Laid-Open No. 6-502162 corresponding to U.S. Pat. No. 5,103,024, and U.S. Pat. No. 5,155,251.

However, these methods using cyanide compounds have raised safety concerns. Namely, toxic alkaline cyanide must be used for obtaining the cyanide compounds, and alcohol containing toxic ammonia gas must be employed to reduce the cyano group. Thus, these methods require complex equipment and are troublesome to carry out.

SUMMARY OF THE INVENTION

It is therefore an object of the present invention to provide synthetic intermediates for HMG-CoA reductase inhibitors, and a method for safely and easily producing such synthetic intermediates.

DESCRIPTION OF THE PREFERRED EMBODIMENTS

As a result of extensive studies in view of the above described problems of the prior art, the present inventors have been first to succeed in synthesizing N-substituted-7-amino-5-hydroxy-3-oxoheptanoic acid derivatives, and have also discovered that important synthetic intermediates for HMG-CoA reductase inhibitors, 6-(2-aminoethyl)-2,2-dimethyl-1,3-dioxane-4-acetic acid esters, can be safely and easily obtained from these derivatives. Furthermore, the present inventors have developed a method for safely and easily producing these novel compounds to achieve this invention.

Accordingly, the present invention provides N- substituted-7-amino-5-hydroxy-3-oxoheptanoic acid derivatives having the general structural formula (1) and a method for producing the same:

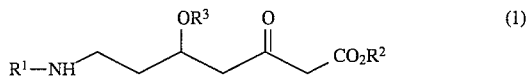

wherein $R^1$ represents a benzyloxycarbonyl group, a lower alkoxycarbonyl group, or a benzoyl group;

$R^2$ represents a lower alkyl group; and $R^3$ represents a hydrogen atom or a protecting group of a hydroxyl group.

The compounds of the present invention are represented by the above general structural formula (1). Examples of the lower alkoxycarbonyl group represented by $R^1$ include carbonyl groups bonding to linear or branched alkoxy radicals having 1 to 4 carbon atoms, such as methoxycarbonyl, ethoxycarbonyl, n-propoxycarbonyl, isopropoxycarbonyl, n-butoxycarbonyl and tert-butoxycarbonyl. Among these, tert-butoxycarbonyl is preferred because it is inexpensive as a starting material. On the other hand, $R^1$ most preferably is benzyloxycarbonyl because it is easy to eliminate the $R^1$ group corresponding to the final protecting amino group in the production of HMG-CoA reductase inhibitors.

Examples of the lower alkyl group represented by $R^2$ in the general structural formula (1) are linear and branched alkyl groups having 1 to 4 carbon atoms, such as methyl, ethyl, n-propyl, isopropyl, n-butyl, isobutyl and tert-butyl. Among these, ethyl group and tert-butyl group are preferred. More preferably, $R^2$ is a tert-butyl group in view of stability in the process for producing HMG-CoA reductase inhibitors.

The protecting group of the hydroxyl group represented by $R^3$ is not particularly limited, and examples thereof are given at pages 10 to 12 of "Protective Group in Organic Synthesis" by Theodora W. Greene (John Wiley & Sons, U.S.A., 1981). Among these, tetrahydropyranyl group (abbreviated as 'THP' below) and tri-substituted silyl groups are preferred. The substituents in the tri-substituted silyl groups are linear and branched alkyl groups having 1 to 4 carbon atoms such as methyl group and tert-butyl group, phenyl group and benzyl group. Examples of the tri-substituted silyl groups are trimethylsilyl, triethylsilyl, isopropyldimethylsilyl, tert-butyldimethylsilyl, tert-butyldiphenylsilyl, triphenylsilyl and tribenzylsilyl.

Since the carbon atom at the 5-position having an —$OR^3$ group in the compound of formula (1) of the present invention is an asymmetric carbon atom, optical isomers having an R- or S-configuration and a racemic modification thereof are within the scope of the compound of formula (1), and the present invention may include all of these.

When the compounds of formula (1) of the present invention are used as synthetic intermediates for HMG-CoA reductase inhibitors, the 5-position of the compound of formula (1) is preferably in an R-configuration to thereby provide a desired optical isomer having excellent pharmaceutical properties, namely, strong antilipemic activity.

The compounds of formula (1) of the present invention can be prepared, for example, according to the following reaction scheme:

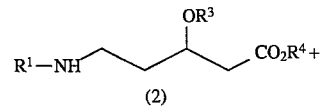

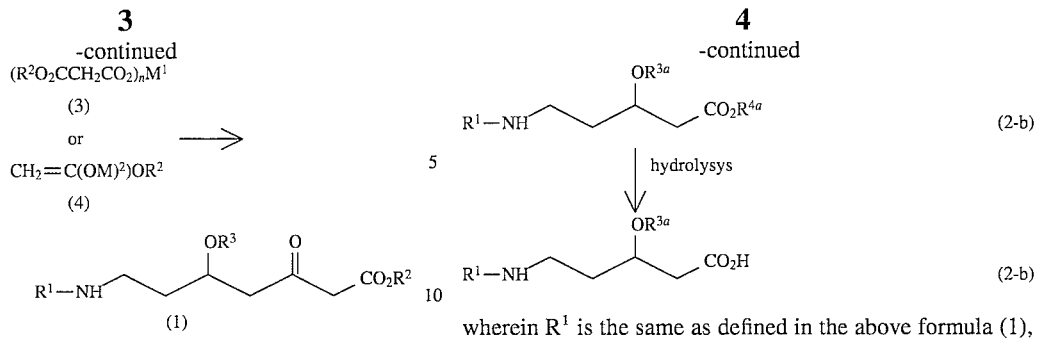

wherein $R^1$, $R^2$ and $R^3$ are the same as defined in the above formula (1), $R^4$ represents a lower alkyl group when $R^3$ is a hydrogen atom, or $R^4$ represents a hydrogen atom or a lower alkyl group when $R^3$ is a protecting group of a hydroxyl group, $M^1$ represents an alkali metal atom (e.g., lithium, sodium and potassium) or an alkaline earth metal atom (e.g., calcium and magnesium), $M^2$ represents an alkali metal atom (e.g., lithium, sodium and potassium), and n is 1 when $M^1$ is an alkali metal atom or n is 2 when $M^1$ is an alkaline earth metal atom.

Thus, the compound (1) of the present invention can be prepared by the condensation of N-substituted-5-amino-3-hydroxypentanoic acid derivatives represented by the above general formula (2) with metal salts of the malonic acid monoester represented by general formula (3) when $R^4$ in formula (2) is a hydrogen atom or with the enolate of the acetic acid ester represented by general formula (4) when $R^4$ represents a lower alkyl group.

The lower alkyl group represented by $R^4$ in the general formula (2) is a linear or a branched alkyl group having 1 to 4 carbon atoms. Examples of the lower alkyl group are methyl, ethyl, n-propyl, isopropyl, n-butyl, isobutyl and tert-butyl. Among these, ethyl group and tert-butyl group are preferred. Since the 3-position carbon atom in the compound of formula (2) is an asymmetric carbon atom, optical isomers having an R- or S-configuration and a racemic modification thereof are within the scope of the compound represented by formula (2), and the present invention can use all of these. However, because the 5-position of the compound of formula (1) preferably has an R-configuration, the 3-position of the compound of formula (2) corresponding to the starting compound of the compound of formula (1) also preferably has an R-configuration.

The above starting compound of formula (2) can be easily synthesized by the following reaction scheme:

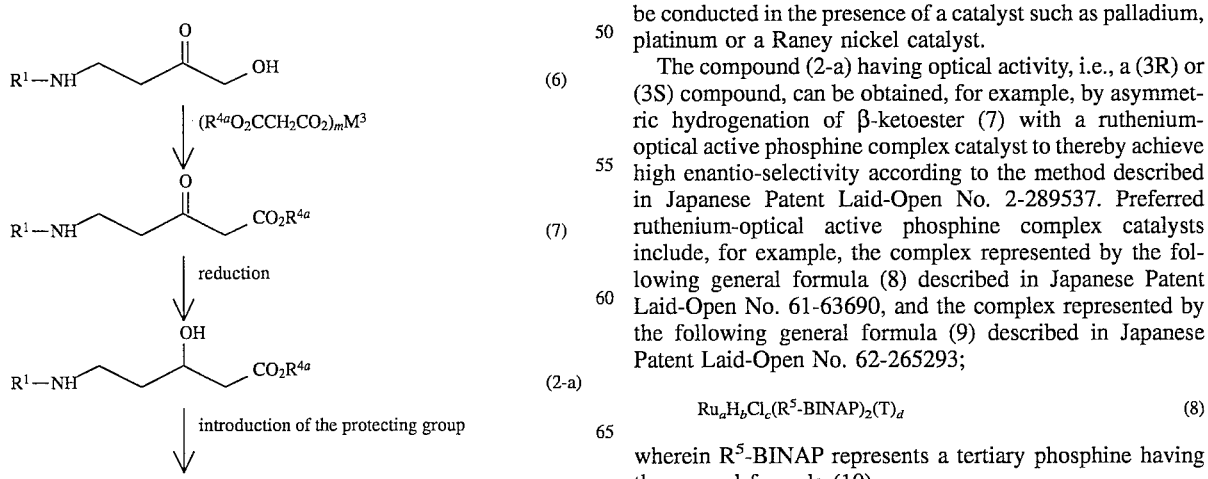

wherein $R^1$ is the same as defined in the above formula (1), $R^{3a}$ represents a protecting group of the hydroxyl group, $R^{4a}$ represents a lower alkyl group, $M^3$ represents an alkali metal atom or an alkaline earth metal atom, and m is 1 when $M^3$ is an alkali metal atom or m is 2 when $M^3$ is an alkaline earth metal atom.

The lower alkyl group represented by $R^{4a}$ preferably is a linear or branched alkyl group having 1 to 4 carbon atoms (e.g., methyl, ethyl, n-propyl, isopropyl, n-butyl, isobutyl and tert-butyl).

As the starting compound (6), a commercial N-substituted-β-alanine can be used as such. Alternatively, the starting compound (6) can be obtained from commercially available β-alanine by introducing the protecting group of the amino group, represented by $R^1$, into the amino group by a conventional method, for example, the reaction of β-alanine with a compound represented by $R^1$—X (wherein $R^1$ is the same as defined above, and X represents a halogen atom), in the presence of a base such as sodium hydroxide. X is preferably a chlorine atom.

In order to obtain β-ketoester (7) from the starting compound (6), a conventional method can be employed. For example, according to the method by T. Nishi et al. (The Journal of Antibiotics, Vol. 47, No. 3, pp. 357–369 (1994)), the condensation of compound (6) with metal salts of the malonic acid monoester represented by $(R^{4a}O_2CCH_2CO_2)_mM^3$ may be carried out in the presence of a reagent for activating an ester such as N,N'-carbonyldiimidazole. Therein, lithium, sodium and potassium atoms are preferred as the alkali metal atom represented by $M^3$, and calcium and magnesium are preferred as the alkaline earth metal atom represented by $M^3$.

In order to obtain the compound (2-a) which is a starting compound of formula (2) of the present invention from β-ketoester (7), a known method for reducing a ketone to an alcohol can be used. For example, reducing agents such as sodium boron hydride, lithium boron hydride, diisopropylaluminum hydride and sodium bis(2-methoxyethoxy) aluminum hydride may be used, or catalytic hydrogenation may be conducted in the presence of a catalyst such as palladium, platinum or a Raney nickel catalyst.

The compound (2-a) having optical activity, i.e., a (3R) or (3S) compound, can be obtained, for example, by asymmetric hydrogenation of β-ketoester (7) with a ruthenium-optical active phosphine complex catalyst to thereby achieve high enantio-selectivity according to the method described in Japanese Patent Laid-Open No. 2-289537. Preferred ruthenium-optical active phosphine complex catalysts include, for example, the complex represented by the following general formula (8) described in Japanese Patent Laid-Open No. 61-63690, and the complex represented by the following general formula (9) described in Japanese Patent Laid-Open No. 62-265293;

wherein $R^5$-BINAP represents a tertiary phosphine having the general formula (10),

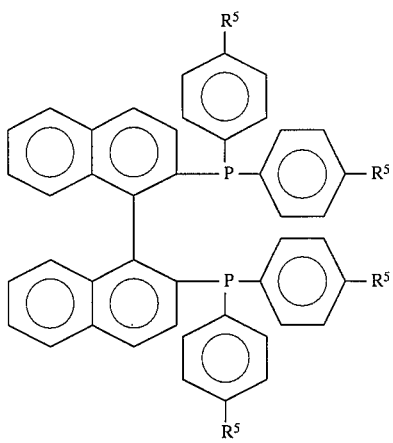 (10)

$R^5$ represents a hydrogen atom, methyl group, tert-butyl group or methoxy group; T represents a tertiary amine; and suffix a is 2, suffix c is 4 and suffix d is 1 when suffix b is 0; or suffix a is 1, suffix c is 1 and suffix d is 0 when suffix b is 1.

$$Ru(R^5\text{-BINAP})(O_2CR^6)_2 \qquad (9)$$

wherein $R^5$-BINAP is the same as defined in formula (8), and $R^6$ represents a lower alkyl group or a trifluoromethyl group.

Examples of the tertiary phosphine compounds represented by the general formula (10) are as follows:
Phosphine 1
  2,2'-bis (diphenylphosphino)-1.1'-binaphthyl (abbreviated as 'BINAP' below);
Phosphine 2
  2,2'-bis[di-(p-tolyl)phosphino]-1.1'-binaphthyl (abbreviated as 'Tol-BINAP' below);
Phosphine 3
  2,2'-bis[di-(p-tert-butylphenyl) phosphino]-1.1'-binaphthyl (abbreviated as 't-Bu-BINAP' below);
Phosphine 4
  2,2'-bis[di-(p-methoxyphenyl) phosphino]-1.1'-binaphthyl (abbreviated as 'Methoxy-BINAP' below).

Since each tertiary phosphine compound has both a (+)-isomer and a (−)-isomer, either isomer may be selected according to the absolute configuration of the objective optical active compound (2-a). Thus, a (+)-isomer is used to obtain the (3R) configuration, or a (−)-isomer for the (3S) configuration.

Examples of useful tertiary amine compounds represented by T in general formula (8) are triethylamine, tributylamine, ethyldiisopropylamine, 1,8-bis(dimethylamino)naphthalene, dimethylaniline, pyridine and N-methylpiperidine. Among these, triethylamine is preferred.

Examples of useful complex compounds represented by general formula (8) are as follows, where the absolute configuration of the tertiary phosphine is not specified:
  Complex 1: $Ru_2Cl_4$ (BINAP)$_2$NEt$_3$;
  Complex 2: $Ru_2Cl_4$ (Tol-BINAP)$_2$NEt$_3$;
  Complex 3: $Ru_2Cl_4$ (t-Bu-BINAP)$_2$NEt$_3$;
  Complex 4: $Ru_2Cl_4$ (Methoxy-BINAP)$_2$NEt$_3$;
  Complex 5: RuHCl (BINAP)$_2$;
  Complex 6: RuHCl (Tol-BINAP)$_2$;
  Complex 7: RuHCl (t-Bu-BINAP)$_2$; and
  Complex 8: RuHCl (Methoxy-BINAP)$_2$;
wherein Et represents an ethyl group.

The lower alkyl group represented by $R^6$ in the general formula (9) is a linear or a branched alkyl group having 1 to 4 carbon atoms. Among these, methyl group is preferred.

Examples of the complex compounds represented by the general formula (9) are as follows, where the absolute configuration of the tertiary phosphine is not specified:
  Complex 9: Ru (BINAP) (O$_2$CCH$_3$)$_2$;
  Complex 10: Ru (Tol-BINAP) (O$_2$CCH$_3$)$_2$;
  Complex 11: Ru (t-Bu-BINAP) (O$_2$CCH$_3$)$_2$;
  Complex 12: Ru (Methoxy-BINAP) (O$_2$CCH$_3$)$_2$;
  Complex 13: Ru (BINAP) (O$_2$CCF$_3$)$_2$;
  Complex 14: Ru (Tol-BINAP) (O$_2$CCF$_3$)$_2$;
  Complex 15: Ru (t-Bu-BINAP) (O$_2$CCF$_3$)$_2$; and
  Complex 16: Ru (Methoxy-BINAP) (O$_2$CCF$_3$)$_2$.

The asymmetric hydrogenation is carried out by dissolving β-ketoester (7) into an alcoholic solvent such as methanol, ethanol or isopropanol, adding the complex (8) or complex (9) in an amount of approximately 0.001 to 0.1 mole, preferably 0.002 to 0.01 mole, per 1 mole of the β-ketoester (7), and completely reacting in a hydrogen atmosphere at a pressure of approximately 5 to 150 atms, preferably 30 to 70 atms, and at a temperature of approximately 25° to 100° C. until the β-ketoester (7) is completely consumed.

For the compound (2-b) in the general formula (2), in which $R^3$ is a protecting group of a hydroxyl group and $R^4$ is a lower alkyl group, a protecting group represented by $R^{3a}$ can be introduced to the hydroxyl group of the compound (2-a). For example, for introducing a THP group, approximately 1 to 1.2 mole of 3,4-dihydro-2H-pyran can be reacted with 1 mole of the compound (2-a) in an organic solvent such as toluene, hexane, heptane, tetrahydrofuran or diethyl ether, in the presence of a catalytic amount of p-toluenesulfonic acid. The temperature for the reaction may range from approximately 20° to 30° C., and the time may range from approximately 2 to 20 hours.

The compound (2-c) having a protecting group of the hydroxyl group represented by $R^3$ and hydrogen as $R^4$ in general formula (2) can also be obtained by hydrolysis of the compound (2-b) with a base such as sodium hydroxide according to conventional methods. When obtaining the compounds (2-b) and (2-c) from the compound (2-a) having optical activity, the compounds (2-b) and (2-c) having optical activity can be obtained by the above method while keeping its absolute configuration.

The compound of formula (1) of the present invention can be obtained by condensing the starting compound (2) with a metal salt of a malonic acid monoester represented by the above formula (3) or an enolate of an acetic acid ester represented by the above formula (4). Examples of useful alkali metal atoms represented by $M^1$ in general formula (3) are lithium, sodium and potassium, and examples of useful alkaline earth metal atoms represented by $M^1$ in general formula (3) are calcium and magnesium.

When the $R^3$ is a protecting group of the hydroxyl group and $R^4$ is a hydrogen atom in the starting compound (2), in other words, when the compound (2) is (2-c), the compound of formula (1) of the present invention can be obtained by condensing the starting compound (2-a) with a metal salt of a malonic acid monoester (3). For example, this reaction can be carried out by dissolving the compound (2-c) in a solvent selected from esters such as ethyl acetate, propyl acetate and butyl acetate, ethers such as tetrahydrofuran and diethyl ether, acetonitrile and mixtures of these solvents, adding an ester activator such as N,N'-carbonyldiimidazole, or a mixed activator consisting of a tertiary amine such as imidazole and a lower alkyl ester of chloroformic acid, wherein the lower alkyl includes linear and branched alkyl having 1 to 4 carbon atoms, in an amount of approximately 0.8 to 1.2 mole, preferably approximately 0.9 to 1.1 mole per 1 mole of the compound (2-c), reacting at room temperature for approximately 30 minutes to 2 hours, cooling to 0° to 10° C., adding approximately 1 to 1.5 equivalent of a metal salt of the malonic acid monoester (3) and 0.9 to 1 mole of magnesium chloride to the compound (2-c), and reacting at approximately 50° to 60° C. for approximately 1 to 3 hours.

When the starting compound (2) is (2-a), in which $R^3$ is a protecting group of a hydroxyl group and $R^4$ is a lower alkyl group, the intended compound (1) can be obtained by a Claisen condensation of the enolate of the acetate ester. Namely, the enolate of the acetate ester can be obtained by reacting an acetate ester represented by $CH_3CO_2R^2$ (where $R^2$ is the same as defined above) with an approximately equimolar amount of an amide represented by $(R^7)_2—NM^2$ (where $M^2$ is the same as defined above, and $R^7$ represents a linear or a branched alkyl group having 1 to 4 carbon atoms) in an organic solvent such as tetrahydrofuran, hexane or diethyl ether at −70° to −40° C. Then, the compound (2-a) and the enolate of the acetate ester in an amount of approximately 1 to 5 equivalents are allowed to react in the same solvent and at the same temperature as above for approximately 1 to 5 hours. The amide represented by $(R^7)_2—NM^2$ can be prepared by reacting a dialkyl amine, for example, diethyl amine, with an alkyl metal represented by $(R^7)_2—M^2$ (where $R^7$ and $M^2$ are the same as defined above) in the same solvent as described above at from approximately 0° C. to ambient (room) temperature for approximately 30 minutes to 1 hour.

When the starting compound (2) is the compound (2-b), in which $R^3$ is a hydrogen atom and $R^4$ is a lower alkyl group, the intended compound (1) can be prepared by condensing the excess enolate of the acetic acid ester with the compound (2-b) at a molar ratio of approximately 2 to 10. The reaction conditions such as solvent and temperature are similar to those for preparing the compound (2-a). According to the present invention, when the compound (2) has optical activity, the compound (1) having optical activity can be obtained while keeping its absolute configuration.

After completing the reaction, the oily final product (1) can be purified by a conventional purification method such as by evaporation of a solvent, extraction and/or silica gel column chromatography.

The compound (1) of the present invention obtained as described above can be easily converted into 6-(2-aminoethyl)-2,2-dimethyl-1,3-dioxane-4-acetic acid ester, an important synthetic intermediate for a HMG-CoA reductase inhibitor, by the following reaction:

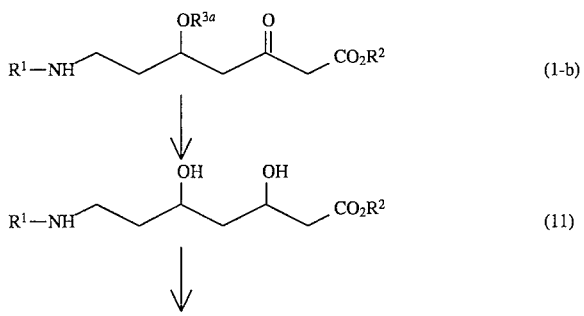

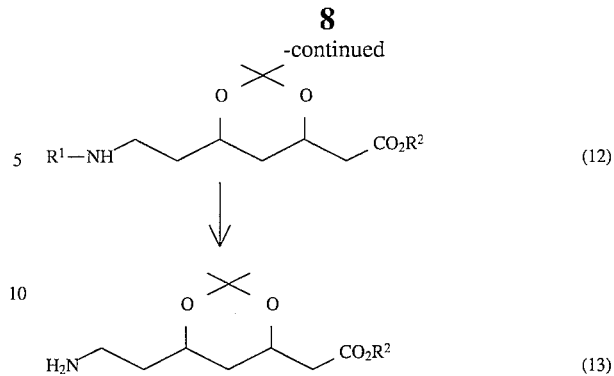

wherein $R^1$, $R^2$ and $R^{3a}$ are the same as defined above.

When $R^3$ is a hydrogen atom in the compound of formula (1) of the present invention, N-substituted-7-amino-3,5-dihydroxyheptanoic acid derivative (11) can be obtained in a conventional method by converting the compound (1) into the compound (1-b) with the protecting group of the hydroxyl group represented by $R^{3a}$; reducing the thus obtained ketone to an alcohol according to the above method for obtaining the compound (2-a) from β-keto ester (7); and eliminating the protecting group of the hydroxyl group by a conventional method. The compound (11) having optical activity at the 3-carbon position, which is reduced, in other words a (3R) or (3S) isomer, can be prepared in high optical purity by asymmetric hydrogenation of the compound (1-b) with a ruthenium-optical-active phosphine complex catalyst (8) or (9) and elimination of the protecting group of the hydroxyl group according to the method described in the above cited Japanese Patent Laid-Open No. 2-289537. When the derivative is used as the synthetic intermediate for a HMG-CoA reductase inhibitor, the 5-position of the compound (1) desirably has an R-configuration in order to obtain the specified optical isomer having excellent pharmaceutical properties. It is desirable that the 3-position of the compound (11) has also an R-configuration. Thus, the compound (11) desirably has the syn-configuration of (3R,5R).

Then, the compound (12) can be obtained by simultaneously protecting the hydroxyl groups at the 3-position and 5-position of the compound (11) as an acetal. Namely, the compound (12) can be obtained by reacting the compound (11) with acetone, 2,2-dimethoxypropane or 2,2-diethoxypropane with a catalytic amount of p-toluenesulfonic acid or sulfuric acid.

The intended compound, 6-(2-aminoethyl)-2,2-dimethyl-1,3-dioxane-4-acetic acid ester (13), can be prepared by eliminating $R^1$, the protecting group of the amino group in the resulting compound (12).

When $R^1$ is a benzyloxycarbonyl group, the compound (13) can be stoichiometrically prepared, for example, by hydrogenation with a palladium-carbon catalyst in a solvent such as ethyl acetate in a hydrogen atmosphere at a pressure of 1 to 25 atms.

The compound of formula (1) of the present invention is a useful synthetic intermediate, which can be easily converted to an important intermediate for a HMG-CoA reductase inhibitor. Details with regard to preparing the HMG-CoA reductase inhibitor and the pharmaceutical properties thereof are given in U.S. Pat. No. 5,003,080 incorporated herein by reference. Furthermore, the compound of formula (1) itself can also be produced according to a safe and easy method.

EXAMPLES

The following Examples illustrate the preferred embodiments of the present invention. However, the scope of this invention should not be construed as being limited to these Examples.

The physical properties of the compounds prepared in these Examples were measure as follows.

A) Chemical Purity, Optical Purity and Diastereoselectivity

Gas Chromatography

Instrument: HP-5890 (made by Hewlett-Packard Co.) with a silicone OV-1 column (made by GL Science Inc.; 0.25 mm×25 mm). Heating program: from 170° to 250° C. at 3° C./min.

Liquid Chromatography

Instrument: L-6000(pump)+L-4000(uv detector) (made by Hitachi, Ltd.)

Column-1: Inertsil ODS-2 (made by GL Science Inc.; particle size 5 μm, 4.6 mm×250 mm). Solvent: acetonitrile/water=70/30. Flow rate: 0.6 ml/min. Wavelength of UV detector: 254 nm.

Column-2: CHIRALCEL OD (made by Daicel Chemical Industries, Ltd.; particle size 5 μm, 4.6 mm×250 mm). Solvent: hexane/isopropanol=95/5. Flow rate: 1.5 ml/min. Wavelength of UV detector: 254 nm.

B) $H^1$-Nuclear Magnetic Resonance Spectrometry:

Instrument: AM-400 (400 MHz) (made by Bruker Inc.).

Internal standard: tetramethylsilane.

C) Optical Rotation:

Instrument: DIP-4 (made by JASCO Inc.).

D) Melting Point:

Instrument: MP-S3 (made by Yanagimoto Shoji K. K.).

Example 1

Synthesis of tert-butyl (5R)-7-benzyloxycarbonylamino-5-hydroxy-3-oxoheptanoate(1)

A: Synthesis of ethyl 5-benzyloxycarbonylamino-3 -oxopentanoate (7)

Into a one-liter four-necked flask were poured 99 g (0.444 mole) of N-benzyloxycarbonyl-β-alanine (made by Kokusan Kagaku) and 600 ml of acetonitrile in a nitrogen stream. Furthermore, 73.4 g (0.453 mole) of N,N'-carbonyldiimidazole was gradually added to the contents of the flask over a period of 15 minutes with gas evolution. Gas evolution was nearly complete after stirring for approximately 30 minutes. The flask was cooled to 10° C., and 113.3 g (0.666 mole) of potassium malonate ethyl ester and then 42.7 g (0.448 mole) of magnesium chloride were separately added to the contents of the flask. The contents were stirred for 1 hour, heated to 50° C., and allowed to react for 2 hours. After acetonitrile was removed by distillation, 350 ml of ethyl acetate and 1 liter of a 5 wt % aqueous hydrochloric acid solution were added to the contents of the flask to thereby adjust the pH to 4. After separating the water layer, the organic layer was neutralized with 100 ml of a 5 wt % aqueous sodium bicarbonate solution, washed with a saturated sodium chloride solution, and then dried with magnesium sulfate. A crude crystal product of 123.4 g was obtained after evaporating the solvent. The crude crystal product was dissolved in a mixture of toluene/hexane=1/2, then 107.3 g (yield: 82.5%) of the intended crystal product (7) having a melting point of 25° to 27° C. was separated at −30° C.

The physical properties of the resulting product are shown as follows:

$H^1$-NMR (CDCl$_3$, δppm): 1.26 (3H,t,J=7.1 Hz), 2.79 (2H,brs), 3.42 (2H,s), 3.45 (2H,brs), 4.15 (2H,q,J=7.1 Hz,14.3 Hz), 5.07 (2H,s), 5.30 (1H,brs), 7.27~7.37 (5H,m)

B: Synthesis of ethyl (3R)-5-benzyloxycarbonylamino-3-hydroxypentanoate (2-a)

Into a 500 ml autoclave, 104.2 g (0.356 mole) of ethyl 5-benzyloxycarbonylamino-3-oxopentanoate (7), obtained by the above process A, 208 ml of ethanol, and 1.202 g (1.423 millimole) of Ru$_2$Cl$_4$[(R)-(+)-BINAP]$_2$NEt$_3$ were poured in a nitrogen stream. After the atmosphere was replaced with hydrogen, hydrogenation was carried out at 50° C. for 20 hours under a hydrogen pressure of 30 atmospheres. After evaporating ethanol, 105.9 g of a crude crystal product was obtained. After recrystallization of the crude product using a toluene/hexane=1/1 solution, 79.1 g (yield: 83%) of the intended crystal product (2-a) having a melting point of 43.5° to 44° C. was obtained.

The physical properties of the resulting product are shown as follows:

Optical Rotation:

$[\alpha]_D^{24}$=−11.0° (c=1, CHCl$_3$) $H^1$-NMR (CDCl$_3$, δppm): 1.25(3H,t,J=7.1 Hz), 1.52~1.72 (2H,m), 2.45 (2H,brs), 3.20~3.24 (1H,m), 3.38~3.48 (1H,m), 3.45 (1H,brs), 4.04~4.10 (1H,m), 4.15 (2H,q,J=7.1 Hz,14.3 Hz), 5.08 (2H,s), 5.44 (1H,brs), 7.29~7.34 (5H, m)

The thus obtained ethyl (3R)-5-benzyloxycarbonyl amino -3-hydroxypentanoate (2-a) was allowed to react with (R)-(+)-α-methoxy-α-trifuluoromethylphenylacetyl chloride to produce an ester. The ester was analyzed by liquid chromatography using the above column-2. The optical purity of ethyl (3R)-5-benzyloxycarbonylamino -3-hydroxypentanoate (2-a) was 99% e.e.

C: Synthesis of tert-butyl (5R)-7-benzyloxycarbonylamino-5-hydroxy-3-oxoheptanoate (1)

Into a 500-ml four-necked flask were poured 19.8 g (0.271 mole) of diethylamine and 50 ml of tetrahydrofuran in a nitrogen stream, and the contents of the flask were then cooled to 0° C. 135 ml of a 15 wt % solution of n-butyl lithium in hexane was added dropwise into the flask. After returning the flask to room temperature, the contents were stirred for 30 min. The contents were then cooled to −40° C., and 31.4 g (0.271 mole) of tert-butyl acetate was added dropwise into the flask. The contents were allowed to react for 1 hour to obtain an enolate at −40° C.

A solution of 20 g (67.8 millimole) of ethyl (3R)-5-benzyloxydicarbonylamino-3-hydroxypentanoate (2-a), obtained by the above process B, dissolved in 20 ml of tetrahydrofuran, was dropwise added to the thus obtained enolate solution, and the contents were allowed to react for 2 hours at −40° C. Water was added while stirring the solution. The solution was then extracted with toluene, and the soluble component of the toluene extraction was washed with a saturated sodium chloride solution and dried with magnesium sulfate. An oily product of 17.5 g was obtained after evaporation of the solvent. The product was purified by passing through a silica gel column using a hexane/ethyl acetate=2/1 as an eluent. This purification provided 14.6 g of the intended oily product (1) in a 48% yield.

The physical properties of the resulting product are shown as follows:

$H^1$-NMR (CDCl$_3$, δppm): 1.46 (9H,s), 1.56~1.71 (2H,m), 2.69 (2H,d,J=5.1 Hz), 3.21~3.51 (3H,m), 3.38 (1H, brs), 3.38 (2H,s), 4.16 (1H,brs), 5.09 (2H,s), 5.21 (1H,brs), 7.30~7.37 (5H,m)

Example 2

Synthesis of tert-butyl (5R)-7-benzyloxycarbonylamino-5-(2-tetrahydropyranyloxy)-3-oxoheptanoate (1)

A: Synthesis of ethyl (3R)-5-benzyloxycarbonylamino-(3-2-tetrahydropyranyloxy)pentanoate (2-b).

Into a 500-ml four-necked flask were poured 50.5 g (0,171 mole) of ethyl (3R)-5-benzyloxycarbonylamino-3-hydroxypentanoate (2-a), obtained by the process B in EXAMPLE 1, 100 ml of toluene and 0.3 g of p-toluenesulfonic acid. Furthermore, 17.3 g (0.205 mole) of 3,4-dihydropyran was gradually added to the contents of the flask over a period of 30 minutes at 25° to 30° C. The contents were allowed to react for 17 hours at the same temperature. After washing the contents with an aqueous sodium bicarbonate solution, the solvent was removed by distillation. As a result, 65.3 g of a crude oily product was obtained. The intended oily product (2-b) was obtained in a yield of 51.1 g (79%) by purifying the crude product with a silica gel column using hexane/ethyl acetate=7/5 as an eluent.

The physical properties of the resulting product are shown as follows:

$H^1$-NMR (CDCl$_3$, δppm): 1.25 (3H,t,J=7.1 Hz), 1.42~2.02 (4H,m), 2.37~2.84 (2H,m), 3.19~4.34 (9H, m), 4.45~4.70 (1H,m), 5.16 (2H,s), 7.28~7.35 (5H,m)

B: Synthesis of (3R)-5-benzyloxycarbonylamino-3-(2-tetrahydropyranyloxy)pentanoic acid (2-c)

Into a 500-ml four-necked flask were poured 61.8 g (0.163 mole) of ethyl (3R)-5-benzyloxycarbonylamino- 3-(2-tetrahydropyranyloxy)pentanoate (2-b) obtained by the above process A and 124 ml of methanol. Then, the contents of the flask were cooled with ice. Furthermore, 72 ml of a 10 wt% aqueous sodium hydroxide solution were added to the contents, and the contents were allowed to completely hydrolyze for 2 hours at the same temperature. Into the solution was added 90 ml of water, and the aqueous mixture was extracted with two 75 ml portions of butyl acetate. 125 ml of toluene and 100 ml of a 5 wt % aqueous hydrochloric acid solution were added to the aqueous layer to thereby adjust the pH to 4.5. The toluene layer was washed with a saturated sodium chloride solution and then dried with magnesium sulfate. After removing the solvent by distillation, 46.9 g (82% yield) of the intended oily product was obtained.

C: Synthesis of tert-butyl (5R)-7-benzyloxycarbonylamino-5-(2-tetrahydropyranyloxy)-3-oxoheptanoate (1)

Into a one-liter four-necked flask were poured 43.9 g (0.125 mole) of (3R)-5-benzyloxycarbonylamino-3-(2-tetrahydropyranyloxy)pentanoic acid (2-c) obtained in the above process B and 290 ml of acetonitrile. Furthermore, 19.6 g (0.121 mole) of N,N'-carbonyldiimidazole was added to the contents over a period of 15 minutes in a nitrogen stream with stirring. Gas evolution was observed. Approximately 30 minutes later the gas evolution was nearly complete. Then, the contents were cooled to approximately 10° C., and 35.2 g (0.178 mole) of potassium malonate tert-butyl ester and next 11.4 g (0.119 mole) of magnesium chloride were separately added thereto. After stirring for 1 hour at the same temperature, the contents were heated to 50° C. and allowed to react for 2 hours. After removing acetonitrile by distillation, 150 ml of ethyl acetate and 200 ml of a 5 wt % aqueous hydrochloric acid solution were added to thereby adjust the pH to 4.5. After separating the aqueous layer, the organic layer was neutralized by adding 25 ml of a 5 wt % aqueous sodium bicarbonate solution. The organic layer was washed with saturated sodium chloride solution and then dried with magnesium sulfate. The solvent was then removed by distillation, to thereby obtain 72.3 g of a crude oily product. The crude product was purified with a silica gel column using hexane/ethyl acetate=1/1 as an eluent to obtain the intended oily product (1). The yield was 57.8 g (79%).

The physical properties of the resulting product are shown as follows:

Optical Rotation: $[\alpha]_D^{24}$=+3.3° (c=1.09, CHCl$_3$)

$H^1$-NMR (CDCl$_3$,δppm): 1.47 (9H,s), 1.59~1.80 (4H,m), 2.59~2.65 (1H,m), 2.89~3.02 (1H,m), 3.19~3.49 (3H, m), 3.38 (1H, brs), 3.79~3.82 (1H,m), 4.17~4.28 (1H, m), 4.49~4.60 (1H,m), 5.08 (2H,s), 7.27~7.36 (5H,m)

Example 3

Synthesis of tert-butyl (5R)-7-benzyloxycarbonylamino-5-(2-tetrahydropyranyloxy)-3-oxoheptanoate (1)

Into a 500-ml four-necked flask were poured 15.4 g (0.211 mole) of diethylamine and 50 ml of tetrahydrofuran. After cooling to 0° C., 135 ml of a 15 wt % solution of n-butyl lithium in hexane was dropwise added into the flask. The contents were stirred for 30 minutes after returning the flask to room temperature. The contents were then cooled to −40° C., and 24.4 g (0.0211 mole) of tert-butyl acetate was dropwise added into the flask. The contents were allowed to react for 1 hour at the same temperature to obtain an enolate.

A solution of 20 g (52.8 millimole) of ethyl (3R)-5-benzyloxycarbonylamino-3-(2-tetrahydropyranyloxy)pentanoate (2-b), obtained by the step A in EXAMPLE 2, dissolved in 20 ml of tetrahydrofuran, was dropwise added to the thus obtained enolate solution, and the contents were allowed to react for 2 hours at the same temperature. Water was added to the contents while stirring, and the solution was extracted with toluene, washed with a saturated sodium chloride solution and dried with magnesium sulfate. The thus obtained crude oily product (17.5 g yield) was purified with a silica gel column using hexane/ethyl acetate=2/1 as an eluent. The intended oily compound (1) was obtained in a yield of 15.2 g (64%).

Reference Example 1

Synthesis of tert-butyl (3R, 5R)-7-benzyloxycrbonylamino-3,5-dihydroxyheptanoate (11)

Into a 500-ml autoclave, 53.0 g (0.118 mole) of tert-butyl (5R)-7-benzyloxycarbonylamino-5-(2-tetrahydropyranyloxy)-3-oxohexanoate (1) obtained by the step C in EXAMPLE 2, 159 ml of methanol, and 0.332 g (0.393 millimole) of Ru$_2$Cl$_4$[(R)-(+)-BINAP]$_2$NEt$_3$ were added in a nitrogen stream. After the atmosphere in the autoclave was replaced with hydrogen, the compound (1) was hydrogenated at 35° C. under a hydrogen pressure of 30 atmospheres for 64 hours. After removing methanol by distillation, 49.1 g of a crude oily product was obtained. The crude product was purified with a silica gel column using hexane/ethyl acetate=2/1 as an eluent to obtain the intended oily product (11). The yield was 36.8 g (85%).

The physical properties of the resulting product are shown as follows:

Optical Rotation: $[\alpha]_D^{24}$=−9.7° (c=1.01, CHCl$_3$)

H$^1$NMR (CDCl$_3$, δppm): 1.45(9H,s), 1.47~1.68 (2H,m), 2.36~2.40 (2H,m), 3.16~3.25 (1H,m), 3.41~3.50 (1H, m), 3.94 (1H, brs ), 4.07 (1H,s), 4.21 (1H,brs), 4.25 (1H,s), 5.09 (2H,s), 5.38 (1H,brs), 7.29~7.35 (5H,m)

The thus obtained tert-butyl (3R, 5R) -7 -benzyloxycarbonylamino-3,5-dihydroxyheptanoate (11) was allowed to react with acetone dimethyl acetal. The resulting acetal derivative was analyzed by gas chromatography. The diastereo-selectivity of the tert-butyl (3R,5R)-7-benzyloxycarbonylamino-3,5-dihydroxyheptanoate (11) was 83% d.e.

Reference Example 2

Synthesis of tert-butyl 4R)-cis-6-benzyloxycrbonylaminoethyl-2,2-dimethyl-1,3-dioxane-4-acetate (12)

Into a 500-ml four-necked flask, 40.0 g (0.109 mole) of tert-butyl (3R,5R)-7-benzyloxycarbonylamino-3,5-dihydroxyheptanoate (11) obtained in REFERENCE EXAMPLE 1, 200 ml of acetone, and 0.4 g of p-toluenesulfonic acid were poured, and allowed to react at 25° to 30° C. for 3 hours. To the contents were added 0.4 g of sodium bicarbonate. After removing acetone by distillation, the contents were extracted with 100 ml of toluene, and washed with two 50 ml portions of water. After removing toluene by distillation, 38.9 g of a crude oily product was obtained. The crude product was purified with a silica gel column using hexane/ethyl acetate=2/1 as an eluent to obtain the intended oily product (12). The yield was 31.1 g (70%).

The physical properties of the resulting product are shown as follows:

H$^1$-NMR (CDCl$_3$, δppm): 1.36 (3H,s), 1.43 (3H,s), 1.44 (9H,s), 1.15~1.27 (1H,m), 1.51~1.73 (3H,m), 2.26~2.44 (2H,m), 3.20~3.39 (2H,m), 3.89~3.97 (1H, m), 4.18~4.27 (1H,m), 5.09 (2H,s), 5.18 (1H,brs), 7.27~7.36 (5H,m)

The thus obtained tert-butyl (4R)-cis-6 -benzyloxycrbonylaminoethyl-2,2-dimethyl-1,3-dioxane-4-acetate (12) was analyzed by gas chromatography. The diastereo-selectivity was 99% d.e.

Reference Example 3

Synthesis of tert-butyl (4F)-cis-6-(2-aminoethyl)-2,2-dimethyl-1,3-dioxane-4-acetate (13)

Into a 500-ml flask, 20.0 g (49.1 millimole) of tert-butyl (4R)-cis-6-benzyloxycrbonylaminoethyl-2,2-dimethyl-1,3-dioxane-4-acetate (12) obtained in REFERENCE EXAMPLE 2 was poured in a nitrogen stream and dissolved in 80 ml of ethyl acetate. After adding 1.0 g of 5 wt % palladium-carbon and replacing the flask atmosphere with hydrogen, hydrogenation was carried out at room temperature under a hydrogen pressure of 1 atmosphere. Hydrogen absorption was completed after 2 hours. Palladium-carbon was removed by filtering with CELITE. After removing ethyl acetate by distillation, 12.1 g (yield 90%) of the intended product (13) having a boiling point of 105° to 113° C. (0.65 mmHg) was obtained by further distillation under reduced pressure.

The physical properties of the resulting product are shown as follows:

Optical Rotation: [α]$_D^{24}$=+15.1° (c=1.45, CHCl$_3$)

H$^1$-NMR (CDCl$_3$, δppm): 1.18~1.29 (1H,s), 1.31 (2H, brs), 1.36 (3H,s), 1.44 (9H,s), 1.45 (3H,s), 1.52~1.68 (3H,m), 2.26~2.46 (2H,s), 2.79 (2H, brs), 3.94~4.03 (1H,m), 4.22~4.29 (1H,m)

Example 4

Synthesis of ethyl (5R)-7-tert-butoxycarbonylamino-5-(2-tetrahydropyranyloxy)-3-oxoheptanoate (1)

A: Synthesis of ethyl 5-tert-butoxycarbonylamino-3-oxopentanoate (7)

The intended compound (1) was prepared in a yield of 89% by a method similar to the process A in EXAMPLE 1, except that N-tert-butoxycarbonyl-β-alanine (6) was used instead of N-benzyloxycarbonyl-β-alanine.

The physical properties of the resulting product are shown as follows:

H$^1$-NMR(CDCl$_3$, δppm): 1.28 (3H,t,J=7.1 Hz), 1.42 (9H, s), 2.78 (2H,t,J=5.7 Hz), 3.36~3.40 (2H,m), 3.45 (2H, s), 4.20 (2H,q,J=7.1 Hz,14.2 Hz), 5.01 (1H,brs)

B: Synthesis of ethyl (3R)-5-tert-butoxycarbonylamino-3-hydroxypentanoate (2-a)

The intended compound (2-a) having an optical purity of 99% e.e. was prepared in a yield of 90% by a method similar to the process B in EXAMPLE 1, except that ethyl 5-tert-butoxycarbonylamino -3- oxopentanoate (7), obtained by the above process A, was used instead of ethyl 5-benzyloxycarbonylamino-3-oxopentanoate (7).

The physical properties of the resulting product are shown as follows:

H$^1$-NMR(CDCl$_3$, δppm): 1.27 (3H,t,J=7.1 Hz), 1.44 (9H, s), 1.54~1.72 (2H,m), 2.47~2.49 (2H,m), 3.15~3.21 (1H,m), 3.51 (1H,m), 4.07~4.13 (1H,m), 4.17 (2H,q, J=7.1 Hz, 14.2 Hz), 5.12 (1H,brs)

C: Synthesis of ethyl (3R) -5-tert-butoxycarbonylamino-3-(2-tetrahydropyranyloxy)-pentanoate (2-b)

The intended compound (2-b) was prepared in a yield of 75% by a method similar to the process A in EXAMPLE 2, except that ethyl (3R)-5-tert-butoxycarbonylamino-3-hydroxypentanoate (2-a), obtained by the above process B, was used instead of ethyl (3R)-5-benzyloxycarbonylamino-3-hydroxypentanoate (2-a).

The physical properties of the resulting product are shown as follows:

H$^1$-NMR(CDCl$_3$, δppm): 1.26 (3H,t,J=7.1 hz), 1.44 (9H, s), 1.49~1.83 (8H,m), 2.44~2.82 (2H,m), 3.18~3.36 (1H,m), 3.45~3.56 (1H,m), 3.34~3.47 (1H,m), 4.14 (2H,q,J=7.1 Hz, 14.2 Hz), 4.15~4.24 (1H,m)

D: Synthesis of tert-butyl (5R)-7-tert-butoxycarbonylamino-5-(2-tetrahydropyranyloxyl)-3-oxoheptanoate (1)

The intended compound (1) was prepared in a yield of 72% by a method similar to the steps B and C in EXAMPLE 2, except that ethyl (3R)-5-tert-butoxycarbonylamino-3-(2-tetrahydropyranyloxy)-pentanoate (2-b), obtained by the above process C, was used instead of ethyl (3R)-5-benzyloxycarbonylamino-3-(2- tetrahydropyranyloxy) pentanoate (2-b) and that potassium malonate ethyl ester was used instead of potassium malonate tert-butyl ester.

The physical properties of the resulting product are shown as follows:

H$^1$—NMR(CDCl$_3$, δppm): 1.27 (3H,t,J=7.1 hz), 1.44 (9H,s), 1.47~1.54 (4H,m), 1.67~1.83 (4H,m), 2.62~3.05 (2H,m), 3.12~3.42 (2H,m), 3.49 (1H,brs), 4.20 (2H,q,J=7.1 Hz, 14.2 Hz), 3.81~4.05 (1H,m)

Reference Example 4

Synthesis of ethyl (3R, 5R)-7-tert-butoxycarbonylamino)-3,5-dihydroxyheptanoate (11)

The intended compound (11) was obtained by a method similar to the above REFERENCE EXAMPLE 1, except that tert-butyl (5R)-7-tert-butoxycarbonylamino-5-(2-tetrahydro-pyranyloxy)-3-oxoheptanoate (1) obtained by the step D in EXAMPLE 4 was used instead of tert-butyl (5R)-7-benzyloxycarbonylamino-5-(2-tetrahydropyranyloxy)-3-oxohexanoate (1). The yield of the product was 75%, and the diastereoselectivity was 89% d.e.

The physical properties of the resulting product are shown as follows:

$H^1$-NMR(CDCl$_3$, δppm): 1.27 (3H,t,J=7.1 Hz), 1.45 (9H, s), 1.47~1.68 (2H,m), 2.38~2.42 (2H,m), 3.18~3.28 (1H,m), 3.43~3.52 (1H,m), 3.96 (1H,brs), 4.09 (1H,s), 4.20 (2H,q,J=7.1 Hz,14.2 Hz), 4.23 (1H,brs), 4.29 (1H,s), 5.41 (1H,brs)

Reference Example 5

Synthesis of ethyl (4R)-cis-6-tert-butoxycarbonylaminoethyl)-2,2-dimethyl-1,3-dioxane-4 acetate (12)

The intended compound (12) was obtained by a method similar to the above REFERENCE EXAMPLE 2, except that ethyl (3R, 5R)-7-tert-butoxycarbonylamino)-3,5-dihydroxyheptanoate (11) obtained in REFERENCE EXAMPLE 4 was used instead of tert-butyl (3R, 5R)-7-benzyloxycarbonylamino-3,5-dihydroxyheptanoate (11). The yield of the product was 70%, and the diastereo-selectivity was 99% d.e.

The physical properties of the resulting product are shown as follows:

$H^1$-NMR(CDCl$_3$, δppm): 1.20~1.29 (1H,m), 1.28 (3H,t, J=7.1 Hz), 1.37 (3H,s), 1.45 (3H,s), 1.44 (9H,s), 1.53~1.69 (4H,m), 2.34~2.57 (2H,m), 3.12~3.30 (2H, m), 3.92~3.99 (1H,m), 4.15 (2H,q, j=7.1 Hz, 14.2 Hz), 4.28~4.35 (1H,m), 4.85 (1H,brs)

Example 5

Synthesis of ethyl (5R)-7-benzoylamino-5-(2-tetrahydropyranyloxy)-3-oxoheptanoate (1)

A: Synthesis of ethyl 5-benzoylamino-3-oxopentanoate (7)

The intended compound (7) was prepared in a yield of 90% by a method similar to the process A in EXAMPLE 1, except that N-benzoyl-β-alanine (6) was used instead of N-benzyloxycarbonyl-β-alanine.

The physical properties of the resulting product are shown as follows:

$H^1$-NMR(CDCl$_3$, δppm): 1.25 (3H,t,J=7.1 Hz), 2.92 (2H, t,J=5.7 Hz), 3.61 (2H,s), 3.71 (1H,q,J=6 Hz,11.5 Hz), 4.18 (2H,q,J=7.1 Hz,13.6 Hz), 6.96 (1H,brs), 7.29~7.49 (3H,m), 7.74~7.76 (2H,m)

B: Synthesis of ethyl (3R)-5-benzoylamino-3-hydroxypentanoate (2-a).

The intended compound (2-a) having an optical purity of 94% e.e. was prepared in a yield of 80% by a method similar to the process B in EXAMPLE 1, except that ethyl 5-benzoylamino-3-oxopentanoate (7), obtained by the above process A, was used instead of ethyl 5-benzyloxycarbonylamino-3-oxopentanoate (7).

The physical properties of the resulting product are shown as follows:

$H^1$-NMR(CDCl$_3$, δppm): 1.27 (3H,t,J=7.1 Hz), 1.78~1.86 (1H,m), 2.47~2.53 (2H,m), 3.40~3.47 (1H,m), 3.79~3.88 (1H,m), 3.99 (1H,d,J=3.4 Hz), 4.17 (2H,q, J=7.1 Hz,14.3 Hz), 7.15 (1H,brs), 7.39~7.48 (3H,m), 7.76~7.79 (2H,m)

C: Synthesis of ethyl (3R)-5-benzoylamino-3-(2-tetrahydropyranyloxy)-pentanoate (2-b)

The intended compound (2-b) was prepared in a yield of 84% by a method similar to the process A in EXAMPLE 2, except that ethyl (3R)-benzoylamino-3-hydroxypentanoate (2-a), obtained by the above process B, was used instead of ethyl (3R)-5-benzyloxycarbonylamino-3-hydroxypentanoate (2a).

The physical properties of the resulting product are shown as follows:

$H^1$-NMR(CDCl$_3$, δppm): 1.26 (3H,t,J=7.1 Hz), 1.52 (4H, brs), 1.71~1.98 (4H,m), 2.44~2.86 (2H,m), 3.43~4.31 (5H,m), 4.15 (2H,q,J=6 Hz, 11.8 Hz), 7.27~7.48 (3H, m), 7.77~7.83 (2H,m)

D: Synthesis of tert-butyl (5R)-7-benzoylamino-5-(2-tetrahydropyranyloxy)-3-oxoheptanoate (1).

The intended compound (1) was prepared in a yield of 74% by a method similar to the processes B and C in EXAMPLE 2, except that ethyl (3R)-benzoylamino-3-(2-tetrahydro-pyranyloxy)-pentanoate (2-b), obtained by the above process C, was used instead of ethyl (3R)-5-benzyloxycarbonylamino-3-(2-tetrahydropyranyloxy)-pentanoate (2-b) and that potassium malonate ethyl ester was used instead of potassium malonate tert-butyl ester.

The physical properties of the resulting product are shown as follows:

$H^1$-NMR(CDCl$_3$, δppm): 1.27 (3H,t,J=7.1 Hz), 1.40~1.98 (8H,m), 2.65~3.12 (2H,m), 3.45 (2H,s), 3.37~4.65 (5H, m), 4.19 (2H,q,J=7.1 Hz,14.3 Hz), 7.40~7.48 (3H,m), 7.77~7.83 (2H,m)

Reference Example 6

Synthesis of ethyl (3R, 5R)-7-benzoylamino-3,5-dihydroxyheptanoate (11)

The intended compound (11) was obtained by a method similar to the above REFERENCE EXAMPLE 1, except that tert-butyl (5R)-7-benzoylamino-5-(2-tetrahydropyranyloxy)-3-oxoheptanoate (1), obtained by the step D in EXAMPLE 5, was used instead of tert-butyl (5R)-7-benzyloxycarbonylamino-5-(2-tetrahydropyranyloxy)-3-oxoheptanoate (1). The yield of the product was 85%, and the diastereomer selectivity was 74% d.e.

The physical properties of the resulting product are shown as follows:

$H^1$-NMR(CDCl$_3$, δppm): 1.27 (3H,t,J=7.1 Hz), 1.57~1.77 (2H,m), 2.42~2.58 (2H,m), 3.30~4.73 (6H,m), 4.15 (2H,q,J=7.1 Hz,9.2 Hz), 7.40~7.50 (3H,m), 7.77~7.79 (2H,m)

Reference Example 7

Synthesis of ethyl (4R)-cis-6-benzoylaminoethyl)-2,2-dimethyl-1,3-dioxane-4 acetate (12)

The intended compound (12) was obtained by a method similar to the above REFERENCE EXAMPLE 2, except that ethyl (3R,5R)-7-benzoylamino)-3,5-dihydroxyheptanoate (11), obtained in REFERENCE EXAMPLE 6, was used instead of tert-butyl (3R, 5R)-7-benzyloxycarbonylamino-3,5-dihydroxyheptanoate (11). The yield of the product was 62%, and the diastereo-selectivity was 99% d.e.

The physical properties of the resulting product are shown as follows:

$H^1$-NMR(CDCl$_3$, δppm): 1.26 (3H,t,J=7.1 Hz), 1.30~1.99 (4H,m), 1.43 (3H,s), 1.48 (3H,s), 2.36~2.57 (2H,m), 3.40~4.39 (5H,m), 7.08 (1H,brs), 7.40~7.48 (3H,m), 7.75~7.77 (2H,m)

It should further be apparent to those skilled in the art that various changes in form and detail of the invention as shown and described above may be made. It is intended that such changes be included within the spirit and scope of the claims appended hereto.

What is claimed is:

1. An N-substituted-7-amino-5-hydroxy-3-oxoheptanoic acid derivative having the general structural formula (1):

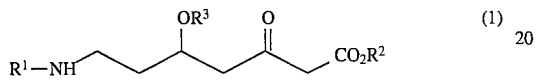

wherein $R^1$ represents a benzyloxycarbonyl group, a lower alkoxycarbonyl group or a benzoyl group; $R^2$ represents a lower alkyl group; and $R^3$ represents a hydrogen atom or a protecting group of a hydroxyl group.

2. A method for producing an N-substituted-7-amino-5-hydroxy-3-oxoheptanoic acid derivative having the general structural formula (1):

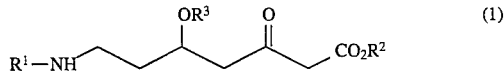

wherein $R^1$ represents a benzyloxycarbonyl group, a lower alkoxycarbonyl group or a benzoyl group; $R^2$ represents a lower alkyl group; and $R^3$ represents a hydrogen atom or a protecting group of a hydroxyl group, comprising the steps of condensing an N-substituted-5-amino-3-hydroxypentanoic acid derivative having the general structural formula (2):

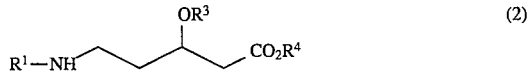

wherein $R^1$, $R^2$ and $R^3$ are the same as defined in the above formula (1); and $R^4$ represents a lower alkyl group when $R^3$ is a hydrogen atom, or $R^4$ represents a hydrogen atom or a lower alkyl group when $R^3$ is a protecting group of a hydroxyl group, with a metal salt of a malonic acid mono-ester having the general structural formula (3) when $R^4$ is a hydrogen atom, or an enolate of an acetic acid ester having the general structural formula (4) when $R^4$ is a lower alkyl group:

$(R^2O_2CCH_2CO_2)_nM^1$ (3)

$(CH_2=C(OM^2)OR^2$ (4)

wherein $R^2$ is the same as defined in the above formula (1); $M^1$ represents an alkali metal atom or an alkali earth metal atom; n is 1 when $M^1$ is an alkali metal atom or n is 2 when $M^1$ is an alkaline earth metal atom; and $M^2$ represents an alkali metal atom.

3. An N-substituted-7-amino-5-hydroxy-3-oxoheptanoic acid derivative as in claim 1, wherein $R^1$ is a lower alkoycarbonyl group.

4. An N-substituted-7-amino-5-hydroxy-3-oxoheptanoic acid derivative as in claim 1, wherein $R^1$ is a benzoxycarbonyl group.

5. An N-substituted-7-amino-5-hydroxy-3-oxoheptanoic acid derivative as in claim 1, wherein $R^2$ is a tert-butyl group.

6. An N-substituted-7-amino-5-hydroxy-3-oxoheptanoic acid derivative as in claim 1, wherein $R^3$ is selected from the group consisting of a tetrahydropyranyl and a trisubstituted silyl group.

7. An N-substituted-7-amino-5-hydroxy-3-oxoheptanoic acid derivative as in claim 1, wherein the compound of formula (1) is an optical isomer having an R- or S-configuration or is a racemic modification thereof.

8. An N-substituted-7-amino-5-hydroxy-3-oxoheptanoic acid derivative as in claim 1, wherein the 5-position of the compound of formula (1) is in an R-configuration.

9. The method of claim 2, wherein the lower alkyl group represented by $R^4$ is selected from the group consisting of an ethyl group and a tert-butyl group.

10. The method of claim 2, wherein the 3-position of the compound of the formula (2) has an R-configuration.

* * * * *